(12) United States Patent
Magal et al.

(10) Patent No.: US 8,166,421 B2
(45) Date of Patent: Apr. 24, 2012

(54) THREE-DIMENSIONAL USER INTERFACE

(75) Inventors: Oz Magal, Ramat Gan (IL); Eran Guendelman, Tel Aviv (IL); Sergio Golman, Tel Aviv (IL); Ziv Hendel, Herzlia (IL); Aviad Maizels, Tel Aviv (IL); Tamir Berliner, Beit Hashmonay (IL); Jonathan Pokras, Bat Yam (IL)

(73) Assignee: Primesense Ltd., Tel Aviv (IL)

( * ) Notice: Subject to any disclaimer, the term of this patent is extended or adjusted under 35 U.S.C. 154(b) by 324 days.

(21) Appl. No.: 12/352,622

(22) Filed: Jan. 13, 2009

(65) Prior Publication Data
US 2009/0183125 A1 Jul. 16, 2009

Related U.S. Application Data

(60) Provisional application No. 61/020,754, filed on Jan. 14, 2008, provisional application No. 61/020,756, filed on Jan. 14, 2008, provisional application No. 61/032,158, filed on Feb. 28, 2008.

(51) Int. Cl.
*G06F 3/033* (2006.01)
*G06F 3/048* (2006.01)
*G06K 9/68* (2006.01)

(52) U.S. Cl. ......... 715/863; 715/850; 715/852; 382/218

(58) Field of Classification Search .................. 715/863, 715/850, 852
See application file for complete search history.

(56) References Cited

U.S. PATENT DOCUMENTS

| 4,550,250 | A | 10/1985 | Mueller et al. |
| 4,988,981 | A | 1/1991 | Zimmerman et al. |
| 5,594,469 | A | 1/1997 | Freeman et al. |
| 5,846,134 | A | 12/1998 | Latypov |
| 5,852,672 | A | 12/1998 | Lu |
| 5,862,256 | A | 1/1999 | Zetts et al. |
| 5,864,635 | A | 1/1999 | Zetts et al. |
| 5,870,196 | A | 2/1999 | Lulli et al. |
| 6,002,808 | A | 12/1999 | Freeman |
| 6,243,054 | B1 | 6/2001 | DeLuca |
| 6,256,033 | B1 | 7/2001 | Nguyen |
| 6,262,740 | B1 | 7/2001 | Lauer et al. |
| 6,345,111 | B1 * | 2/2002 | Yamaguchi et al. .......... 382/118 |

(Continued)

FOREIGN PATENT DOCUMENTS

WO 9935633 A2 7/1999

(Continued)

OTHER PUBLICATIONS

Hart, D., U.S. Appl. No. 09/616,606 "Method and System for High Resolution , Ultra Fast 3-D Imaging" filed on Jul. 14, 2000.

(Continued)

*Primary Examiner* — William Bashore
*Assistant Examiner* — David Phantana Angkool
(74) *Attorney, Agent, or Firm* — D. Kliger IP Services Ltd.

(57) ABSTRACT

A user interface method includes defining an interaction surface containing an interaction region in space. A sequence of depth maps is captured over time of at least a part of a body of a human subject. The depth maps are processed in order to detect a direction and speed of movement of the part of the body as the part of the body passes through the interaction surface. A computer application is controlled responsively to the detected direction and speed.

19 Claims, 4 Drawing Sheets

U.S. PATENT DOCUMENTS

| | | | |
|---|---|---|---|
| 6,345,893 | B2 | 2/2002 | Fateh et al. |
| 6,452,584 | B1 | 9/2002 | Walker et al. |
| 6,559,813 | B1 | 5/2003 | DeLuca et al. |
| 6,681,031 | B2 | 1/2004 | Cohen et al. |
| 6,686,921 | B1 | 2/2004 | Rushmeier et al. |
| 6,690,370 | B2* | 2/2004 | Ellenby et al. ............... 345/419 |
| 6,741,251 | B2 | 5/2004 | Malzbender |
| 6,857,746 | B2 | 2/2005 | Dyner |
| 6,977,654 | B2 | 12/2005 | Malik et al. |
| 7,003,134 | B1 | 2/2006 | Covell et al. |
| 7,013,046 | B2 | 3/2006 | Kawamura et al. |
| 7,042,440 | B2 | 5/2006 | Pryor et al. |
| 7,042,442 | B1 | 5/2006 | Kanevsky et al. |
| 7,170,492 | B2 | 1/2007 | Bell |
| 7,215,815 | B2 | 5/2007 | Honda |
| 7,227,526 | B2* | 6/2007 | Hildreth et al. .............. 345/156 |
| 7,259,747 | B2 | 8/2007 | Bell |
| 7,264,554 | B2* | 9/2007 | Bentley ........................ 473/222 |
| 7,289,227 | B2* | 10/2007 | Smetak et al. ................ 356/614 |
| 7,302,099 | B2 | 11/2007 | Zhang et al. |
| 7,333,113 | B2* | 2/2008 | Gordon ........................ 345/475 |
| 7,340,077 | B2 | 3/2008 | Gokturk et al. |
| 7,348,963 | B2 | 3/2008 | Bell |
| 7,358,972 | B2* | 4/2008 | Gordon et al. ................ 345/473 |
| 7,370,883 | B2* | 5/2008 | Basir et al. .................... 280/735 |
| 7,428,542 | B1 | 9/2008 | Fink et al. |
| 7,474,256 | B2* | 1/2009 | Ohta et al. .................... 342/146 |
| 7,536,032 | B2 | 5/2009 | Bell |
| 7,573,480 | B2* | 8/2009 | Gordon ........................ 345/475 |
| 7,576,727 | B2 | 8/2009 | Bell |
| 7,580,572 | B2 | 8/2009 | Bang et al. |
| 7,688,998 | B2* | 3/2010 | Tuma et al. ................... 382/103 |
| 7,696,876 | B2* | 4/2010 | Dimmer et al. ............ 340/572.1 |
| 7,812,842 | B2* | 10/2010 | Gordon ........................ 345/475 |
| 7,821,541 | B2 | 10/2010 | Delean |
| 7,840,031 | B2* | 11/2010 | Albertson et al. ............ 382/103 |
| 7,925,549 | B2 | 4/2011 | Looney et al. |
| 2002/0071607 | A1 | 6/2002 | Kawamura et al. |
| 2003/0057972 | A1 | 3/2003 | Pfaff et al. |
| 2003/0088463 | A1 | 5/2003 | Kanevsky |
| 2003/0156756 | A1 | 8/2003 | Gokturk et al. |
| 2003/0235341 | A1 | 12/2003 | Gokturk et al. |
| 2004/0174770 | A1 | 9/2004 | Reed |
| 2004/0183775 | A1 | 9/2004 | Bell |
| 2004/0184640 | A1 | 9/2004 | Bang et al. |
| 2004/0184659 | A1 | 9/2004 | Bang et al. |
| 2005/0031166 | A1 | 2/2005 | Fujimara et al. |
| 2005/0088407 | A1 | 4/2005 | Bell et al. |
| 2005/0089194 | A1 | 4/2005 | Bell |
| 2005/0110964 | A1 | 5/2005 | Bell et al. |
| 2005/0122308 | A1 | 6/2005 | Bell et al. |
| 2005/0162381 | A1 | 7/2005 | Bell et al. |
| 2005/0265583 | A1 | 12/2005 | Covell et al. |
| 2006/0010400 | A1 | 1/2006 | Dehlin et al. |
| 2006/0092138 | A1 | 5/2006 | Kim et al. |
| 2006/0115155 | A1 | 6/2006 | Lui et al. |
| 2006/0149737 | A1 | 7/2006 | Du et al. |
| 2006/0159344 | A1 | 7/2006 | Shao et al. |
| 2007/0154116 | A1 | 7/2007 | Shieh |
| 2007/0230789 | A1 | 10/2007 | Chang et al. |
| 2008/0062123 | A1 | 3/2008 | Bell |
| 2008/0094371 | A1 | 4/2008 | Forstall et al. |
| 2008/0123940 | A1 | 5/2008 | Kundu et al. |
| 2008/0150890 | A1 | 6/2008 | Bell et al. |
| 2008/0150913 | A1 | 6/2008 | Bell et al. |
| 2008/0170776 | A1* | 7/2008 | Albertson et al. ............ 382/154 |
| 2008/0236902 | A1 | 10/2008 | Imaizumi |
| 2008/0252596 | A1 | 10/2008 | Bell et al. |
| 2008/0256494 | A1 | 10/2008 | Greenfield |
| 2008/0260250 | A1 | 10/2008 | Vardi |
| 2009/0009593 | A1 | 1/2009 | Cameron et al. |
| 2009/0027335 | A1 | 1/2009 | Ye |
| 2009/0077504 | A1 | 3/2009 | Bell |
| 2009/0078473 | A1 | 3/2009 | Overgard et al. |
| 2009/0083122 | A1 | 3/2009 | Angell et al. |
| 2009/0083622 | A1 | 3/2009 | Chien et al. |
| 2009/0096783 | A1 | 4/2009 | Shpunt et al. |
| 2009/0183125 | A1 | 7/2009 | Magal et al. |
| 2009/0195392 | A1 | 8/2009 | Zalewski |
| 2009/0297028 | A1 | 12/2009 | De Haan |
| 2010/0002936 | A1 | 1/2010 | Khomo |
| 2010/0007717 | A1 | 1/2010 | Spektor et al. |
| 2010/0034457 | A1 | 2/2010 | Berliner et al. |
| 2010/0036717 | A1 | 2/2010 | Trest |
| 2011/0018795 | A1* | 1/2011 | Jang ............................. 345/156 |
| 2011/0193939 | A1* | 8/2011 | Vassigh et al. ................. 348/46 |

FOREIGN PATENT DOCUMENTS

| | | | |
|---|---|---|---|
| WO | 03071410 | A2 | 8/2003 |
| WO | 2004107272 | A1 | 12/2004 |
| WO | 2005003948 | A1 | 1/2005 |
| WO | 2005094958 | A1 | 10/2005 |
| WO | 2007043036 | A2 | 4/2007 |
| WO | 2007078639 | A1 | 7/2007 |
| WO | 2007105205 | A2 | 9/2007 |
| WO | 2007132451 | A2 | 11/2007 |
| WO | 2007135376 | A2 | 11/2007 |
| WO | 2008120217 | A2 | 10/2008 |

OTHER PUBLICATIONS

International Application PCT/IL2007/000306 Search Report dated Oct. 2, 2008.

Litvak et al., U.S. Appl. No. 61/308,996 "Detection, Segmentation and Tracking of Hands by Fusion of Color and Depth Video Streams" filed Mar. 1, 2010.

International Application PCT/IL2006/000335 Preliminary Report on Patentability dated Apr. 24, 2008.

Avidan et al., "Trajectory triangulation: 3D reconstruction of moving points from amonocular image sequence", IEEE Transactions on Pattern Analysis and Machine Intelligence (PAMI), vol. 22, No. 4, pp. 348-3537, Apr. 2000.

Leclerc et al., "The direct computation of height from shading", The Proceedings of the IEEE Computer Society Conference on Computer Vision and Pattern Recognition (CVPR), pp. 552-558, USA, Jun. 1991.

Zhang et al., "Shape from intensity gradient", IEEE Transactions on Systems, Man and Cybernetics—Part A: Systems and Humans, vol. 29, No. 3, pp. 318-325, May 1999.

Zhang et al., "Height recovery from intensity gradients", IEEE Computer Society Conference on Computer Vision and Pattern Recognition (CVPR), pp. 508-513, Jun. 21-23, 1994.

Horn, B., "Height and gradient from shading", International Journal of Computer Vision, vol. 5, No. 1, pp. 37-76, Aug. 1990.

Bruckstein, A., "On shape from shading", Computer Vision, Graphics & Image Processing, vol. 44, pp. 139-154, year 1988.

Zhang et al., "Rapid Shape Acquisition Using Color Structured Light and Multi-Pass Dynamic Programming", 1st International Symposium on 3D Data Processing Visualization and Transmission (3DPVT), Italy, Jul. 2002.

Besl, P., "Active, Optical Range Imaging Sensors", Machine vision and applications, vol. 1, pp. 127-152, year 1988.

Horn et al., "Toward optimal structured light patterns", Proceedings of International Conference on Recent Advances in 3D Digital Imaging and Modeling, pp. 28-37, Ottawa, Canada, May 1997.

Goodman, J.W., "Statistical Properties of Laser Speckle Patterns", Laser Speckle and Related Phenomena, pp. 9-75, Springer-Verlag, Berlin Heidelberg, 1975.

Asada et al., "Determining Surface Orientation by Projecting a Stripe Pattern", IEEE Transactions on Pattern Analysis and Machine Intelligence (PAMI), vol. 10, No. 5, pp. 749-754, Sep. 1988.

Winkelbach et al., "Shape from Single Stripe Pattern Illumination", Luc Van Gool (Editor), (DAGM 2002), Lecture Notes in Computer Science 2449, p. 240-247, Springer 2002.

Koninckx et al., "Efficient, Active 3D Acquisition, based on a Pattern-Specific Snake", Luc Van Gool (Editor), (DAGM 2002), Lecture Notes in Computer Science 2449, pp. 557-565, Springer 2002.

Kimmel et al., "Analyzing and synthesizing images by evolving curves with the Osher-Sethian method", International Journal of Computer Vision, vol. 24, No. 1, pp. 37-56, year 1997.

Zigelman et al., "Texture mapping using surface flattening via multi-dimensional scaling", IEEE Transactions on Visualization and Computer Graphics, vol. 8, No. 2, pp. 198-207, Apr. 2002.

Dainty, J.C., "Introduction", Laser Speckle and Related Phenomena, pp. 1-7, Springer-Verlag, Berlin Heidelberg, 1975.

Mendlovic et al., "Composite harmonic filters for scale, projection and shift invariant pattern recognition", Applied Optics Journal, vol. 34, No. 2, Jan. 10, 1995.

Cheng et al., "Articulated Human Body Pose Inference from Voxel Data Using a Kinematically Constrained Gaussian Mixture Model", CVPR EHuM2: 2nd Workshop on Evaluation of Articulated Human Motion and Pose Estimation, 2007.

Brand, M., U.S. Appl. No. 12/762,336 "Remote Text Input Using Handwriting" filed Apr. 18, 2010.

Shadmi, A., U.S. Appl. No. 12/683,452 "Three-Dimensional User Interface" filed on Jan. 7, 2010.

Sali, E., U.S. Appl. No. 61/223,502 "Gesture Recognition Method & System" filed Aug. 13, 2009.

Dekker, L., "Building Symbolic Information for 3D Human Body Modeling from Range Data", Proceedings of the Second International Conference on 3D Digital Imaging and Modeling, IEEE computer Society, pp. 388-397, 1999.

Holte et al., "Gesture Recognition using a Range Camera", Technical Report CVMT-07-01 ISSN 1601-3646, Feb. 2007.

Li et al., "Real-Time 3D Motion Tracking with Known Geometric Models", Real-Time Imaging Journal, vol. 5, pp. 167-187, Academic Press 1999.

International Application PCT/IL2007/000574 Search Report dated Sep. 10, 2008.

Segen et al., Shadow gestures: 3D hand pose estimation using a single camera, Proceedings of IEEE International Conference on Computer Vision and Pattern Recognition, pp. 479-485, Fort Collins, USA, 1999.

Vogler et al., "ASL recognition based on a coupling between HMMs and 3D motion analysis", Proceedings of IEEE International Conference on Computer Vision, pp. 363-369, Mumbai, India, 1998.

Nam et al., "Recognition of Hand Gestures with 3D, Nonlinear Arm Movements", Pattern Recognition Letters, vol. 18/01, pp. 105-113, 1997.

Segen et a;., "Human-computer interaction using gesture recognition and 3D hand tracking", ICIP 98, Proceedings of the IEEE International Conference on Image Processing, vol. 3, pp. 188-192, Oct. 4-7, 1998.

Nesbat, S., "A System for Fast, Full-Text Entry for Small Electronic Devices", Proceedings of the 5th International Conference on Multimodal Interfaces, ICMI 2003, Vancouver, Nov. 5-7, 2003.

International Application PCT/IL2007/000574 Patentability Report dated Mar. 19, 2009.

Fua et al., "Human Shape and Motion Recovery Using Animation Models", 19th Congress, International Society for Photogrammetry and Remote Sensing, Amsterdam, The Netherlands, Jul. 2000.

Allard et al., "Marker-less Real Time 3D modeling for Virtual Reality", Immersive Projection Technology, IPT 2004, Iowa State University.

Howe et al., "Bayesian Reconstruction of 3D Human Motion from Single-Camera Video", Advanced in Neural Information Processing Systems 12, Denver, Colorado 1999.

Li et al., "Real-Time 3D Motion Recognition with Dense Depth Map", Report CPSC525, Department of Computer Science, University of British Columbia, Vancouver BC 2004.

Grammalidis et al., "3-D Human Body Tracking from Depth Images Using Analysis by Synthesis", Proceedings of the IEEE International Conference on Image Processing (ICIP2001), Thessaloniki, Greece, pp. 185-188.

Maizels et al., U.S. Appl. No. 61/159,808 "Interfaces for 3D Based Man-Machine Interaction" filed on Mar. 13, 2009.

Ascension Technology Corporation, "Flock of Birds: Real-Time Motion Tracking", 2008.

Bleiwess et al., "Fusing Time-of-Flight Depth and Color for Real-Time Segmentation and Tracking", Dyn3D 2009, Lecture Notes in Computer Science 5742, pp. 58-69, Jena, Germany, Sep. 9, 2009.

Bleiwess et al., "Markerless Motion Capture Using a Single Depth Sensor", SIGGRAPH Asia 2009, Yokohama, Japan, Dec. 16-19, 2009.

Bevilacqua et al., "People Tracking Using a Time-Of-Flight Depth Sensor", Proceedings of the IEEE International Conference on Video and Signal Based Surveillance, Sydney, Australia, Nov. 22-24, 2006.

Bradski, G., "Computer Vision Face Tracking for Use in a Perceptual User Interface", Intel Technology Journal, vol. 2, issue 2 (2nd Quarter 2008).

Comaniciu et al., "Kernel-Based Object Tracking", IEEE Transactions on Pattern Analysis and Machine Intelligence, vol. 25, No. 5, pp. 564-577, May 2003.

Gesturetec Inc., "Gesture Control Solutions for Consumer Devices", Canada, 2009.

Gokturk et al., "A Time-Of-Flight Depth Sensor—System Description, Issues and Solutions", Proceedings of the 2004 Conference on Computer Vision and Patter Recognition Workshop (CVPRW'04), vol. 3, pp. 35, Jun. 27-Jul. 2, 2004.

Grest et al., "Single View Motion Tracking by Depth and Silhouette Information", SCIA 2007—Scandinavian Conference on Image Analysis, Lecture Notes in Computer Science 4522, pp. 719-729, Aalborg, Denmark, Jun. 10-14, 2007.

Haritaoglu et al., "Ghost 3d: Detecting Body Posture and Parts Using Stereo", Proceedings of the IEEE Workshop on Motion and Video Computing (MOTION'02), pp. 175-180, Orlando, USA, Dec. 5-6, 2002.

Haritaoglu et al., "W4S : A real-time system for detecting and tracking people in 2<1/2>D", ECCV 98—5th European conference on computer vision, vol. 1407, pp. 877-892, Freiburg , Germany, Jun. 2-6, 1998.

Harville, M., "Stereo Person Tracking with Short and Long Term Plan-View Appearance Models of Shape and Color", Proceedings of the IEEE International Conference on Advanced Video and Signal-Based Surveillance (AVSSS-2005), pp. 522-527, Como, Italy, Sep. 15-16, 2005.

Holte, M., "Fusion of Range and Intensity Information for View Invariant Gesture Recognition", IEEE Conference on Computer Vision and Pattern Recognition Workshops (CVPRW '08), pp. 1-7, Anchorage, USA, Jun. 23-28, 2008.

Kaewtrakulpong et al., "An Improved Adaptive Background Mixture Model for Real-Time Tracking with Shadow Detection", Proceedings of the 2nd European Workshop on Advanced Video Based Surveillance Systems (AVBS'01), Kingston, UK, Sep. 2001.

Kolb et al., "ToF-Sensors: New Dimensions for Realism and Interactivity", Proceedings of the IEEE Conference on Computer Vision and Patter Recognition Workshops, pp. 1-6, Anchorage, USA, Jun. 23-28, 2008.

Kolsch et al., "Fast 2D Hand Tracking with Flocks of Features and Multi-Cue Integration", IEEE Workshop on Real-Time Vision for Human Computer Interaction (at CVPR'04), Washington, USA, Jun. 27-Jul. 2, 2004.

Krumm et al., "Multi-Camera Multi-Person Tracking for EasyLiving", 3rd IEEE International Workshop on Visual Surveillance, Dublin, Ireland, Jul. 1, 2000.

Leens et al., "Combining Color, Depth, and Motion for Video Segmentation", ICVS 2009—7th International Conference on Computer Vision Systems, Liege, Belgium Oct. 13-15, 2009.

MacCormick et al., "Partitioned Sampling, Articulated Objects, and Interface-Quality Hand Tracking", ECCV '00—Proceedings of the 6th European Conference on Computer Vision-Part ll , pp. 3-19, Dublin, Ireland, Jun. 26-Jul. 1, 2000.

Malassiotis et al., "Real-Time Hand Posture Recognition Using Range Data", Image and Vision Computing, vol. 26, No. 7, pp. 1027-1037, Jul. 2, 2008.

Morano et al., "Structured Light Using Pseudorandom Codes", IEEE Transactions on Pattern Analysis and Machine Intelligence, vol. 20, issue 3, pp. 322-327, Mar. 1998.

Munoz-Salinas et al., "People Detection and Tracking Using Stereo Vision and Color", Image and Vision Computing, vol. 25, No. 6, pp. 995-1007, Jun. 1, 2007.

Nanda et al., "Visual Tracking Using Depth Data", Proceedings of the 2004 Conference on Computer Vision and Patter Recognition Workshop, vol. 3, Washington, USA, Jun. 27-Jul. 2, 2004.

Scharstein et al., "High-Accuracy Stereo Depth Maps Using Structured Light", IEEE Conference on Computer Vision and Patter Recognition, vol. 1, pp. 195-2002, Madison, USA, Jun. 2003.

Shi et al., "Good Features to Track", IEEE Conference on Computer Vision and Pattern Recognition, pp. 593-600, Seattle, USA, Jun. 21-23, 1994.

Siddiqui et al., "Robust Real-Time Upper Body Limb Detection and Tracking", Proceedings of the 4th ACM International Workshop on Video Surveillance and Sensor Networks, Santa Barbara, USA, Oct. 27, 2006.

Softkinetic S.A., IISU™—3D Gesture Recognition Platform for Developers of 3D Applications, Belgium, Brussels, 2007-2010.

Sudderth et al., "Visual Hand Tracking Using Nonparametric Belief Propagation", IEEE Workshop on Generative Model Based Vision at CVPR'04, Washington, USA, Jun. 27-Jul. 2, 2004.

Tsap, L., "Gesture-Tracking in Real Time with Dynamic Regional Range Computation", Real-Time Imaging, vol. 8, issue 2, pp. 115-126, Apr. 2002.

Xu et al., "A Multi-Cue-Based Human Body Tracking System", Proceedings of the 5ths International Conference on Computer Vision Systems (ICVS 2007), Germany, Mar. 21-24, 2007.

Xu et al., "Human Detecting Using Depth and Gray Images", Proceedings of the IEE Conference on Advanced Video and Signal Based Surveillance (AVSS'03), Miami, USA, Jul. 21-22, 2003.

Yilmaz et al., "Object Tracking: A Survey", ACM Computing Surveys, vol. 38, No. 4, article 13, Dec. 2006.

Zhu et al., "Controlled Human Pose Estimation From Depth Image Streams", IEEE Conference on Computer Vision and Patter Recognition Workshops, pp. 1-8, Anchorage, USA, Jun. 23-27, 2008.

International Application PCT/IB2010/051055 Search Report dated Sep. 1, 2010.

La Viola, J. Jr., "Whole-Hand and Speech Input in Virtual Environments", Computer Science Department, Florida Atlantic University, USA, 1996.

Martell, C., "Form: An Experiment in the Annotation of the Kinematics of Gesture", Dissertation, Computer and Information Science, University of Pennsylvania, 2005.

Galor et al., U.S. Appl. No. 61/386,591 "Virtual keyboard for text input" filed on Sep. 27, 2010.

Sali, E., U.S. Appl. No. 61/349,894 "Depth sensor with application interface" filed May 31, 2010.

Hoggnung et al., U.S. Appl. No. 61/355,574 "Gesture based user interface models: SoftBar/SoftPad" filed on Jun. 17, 2010.

Prime Sense Inc., "Prime Sensor™ NITE 1.1 Framework Programmer's Guide", Version 1.2, year 2009.

U.S. Appl. No. 61/523,404, filed Aug. 15, 2011.

U.S. Appl. No. 61/504,339, filed Jul. 5, 2011.

U.S. Appl. No. 61/521,448, filed Aug. 9, 2011.

U.S. Appl. No. 61/523,349, filed Aug. 14, 2011.

Primesense, "Natural Interaction", YouTube Presentation, Jun. 9, 2010 http://www.youtube.com/watch?v=TzLKsex43zI~.

International Application PCT/IB2011/053192 filed on Jul. 18, 2011.

* cited by examiner

THREE-DIMENSIONAL USER INTERFACE

CROSS-REFERENCE TO RELATED APPLICATIONS

This application claims the benefit of U.S. Provisional Patent Applications 61/020,754 and 61/020,756, filed Jan. 14, 2008, and of U.S. Provisional Patent Application 61/032,158, filed Feb. 28, 2008, all of which are incorporated herein by reference.

FIELD OF THE INVENTION

The present invention relates generally to user interfaces for computerized systems, and specifically to user interfaces that are based on three-dimensional sensing.

BACKGROUND OF THE INVENTION

Many different types of user interface devices and methods are currently available. Common tactile interface devices include the computer keyboard, mouse and joystick. Touch screens detect the presence and location of a touch by a finger or other object within the display area. Infrared remote controls are widely used, and "wearable" hardware devices have been developed, as well, for purposes of remote control.

Computer interfaces based on three-dimensional (3D) sensing of parts of the user's body have also been proposed. For example, PCT International Publication WO 03/071410, whose disclosure is incorporated herein by reference, describes a gesture recognition system using depth-perceptive sensors. A 3D sensor provides position information, which is used to identify gestures created by a body part of interest. The gestures are recognized based on the shape of the body part and its position and orientation over an interval. The gesture is classified for determining an input into a related electronic device.

As another example, U.S. Pat. No. 7,348,963, whose disclosure is incorporated herein by reference, describes an interactive video display system, in which a display screen displays a visual image, and a camera captures 3D information regarding an object in an interactive area located in front of the display screen. A computer system directs the display screen to change the visual image in response to the object.

SUMMARY OF THE INVENTION

Embodiments of the present invention that are described hereinbelow provide improved methods and systems for user interaction with a computer system based on 3D sensing of parts of the user's body. In some of these embodiments, the combination of 3D sensing with a visual display creates a sort of "touchless touch screen," enabling the user to select and control objects appearing on the display without actually touching the display.

There is therefore provided, in accordance with an embodiment of the present invention, a user interface method that includes defining an interaction surface containing an interaction region in space. A sequence of depth maps is captured over time of at least a part of a body of a human subject. The depth maps are processed in order to detect a direction and speed of movement of the part of the body as the part of the body passes through the interaction surface. A computer application is controlled responsively to the detected direction and speed.

In some embodiments, controlling the computer application includes displaying an object on a display screen, and changing the displayed object responsively to the movement of the part of the body. Displaying the object may include displaying a touch point on the screen representing a location of the part of the body in the interaction region. Additionally or alternatively, the method includes defining a visualization surface containing a visualization region in the space, such that the interaction surface is within the visualization region, and processing the depth maps in order to identify the part of the body that is located within the visualization region, wherein displaying the object includes presenting on the display screen a representation of the part of the body that is located within the visualization region. Further additionally or alternatively, defining the interaction surface includes specifying dimensions of the interaction surface, and mapping the interaction surface to the display screen responsively to the specified dimensions.

In a disclosed embodiment, processing the depth maps includes applying a three-dimensional connected component analysis to the depth maps in order to identify the part of the body. Additionally or alternatively, processing the depth maps includes predicting a location of the part of the body responsively to the movement, and controlling the computer application includes generating a control input to the computer application responsively to the predicted location.

Optionally, processing the depth maps includes identifying, responsively to the detected movement, a gesture made by the human subject. Identifying the gesture may include learning the gesture during a training phase, and thereafter detecting the learned gesture in order to control the computer application.

In one embodiment, processing the depth maps includes identifying, responsively to the detected movement, a collision induced by the movement with a predefined three-dimensional shape in space. In another embodiment, processing the depth maps includes identifying a posture of at least the part of the body, and controlling the computer application responsively to the posture.

There is also provided, in accordance with an embodiment of the present invention, user interface apparatus, including a sensing device, which is configured to capture a sequence of depth maps over time of at least a part of a body of a human subject. A processor is configured to process the depth maps in order to detect a direction and speed of movement of the part of the body as the part of the body passes through a predefined interaction surface, which contains an interaction region in space, and to control a computer application responsively to the detected direction and speed.

There is additionally provided, in accordance with an embodiment of the present invention, a computer software product, including a computer-readable medium in which program instructions are stored, which instructions, when read by a computer, cause the computer to process a sequence of depth maps created over time of at least a part of a body of a human subject in order to detect a direction and speed of movement of the part of the body as the part of the body passes through a predefined interaction surface, which contains an interaction region in space, and to control a computer application responsively to the detected direction and speed.

The present invention will be more fully understood from the following detailed description of the embodiments thereof, taken together with the drawings in which:

DETAILED DESCRIPTION OF EMBODIMENTS

Figure 1:
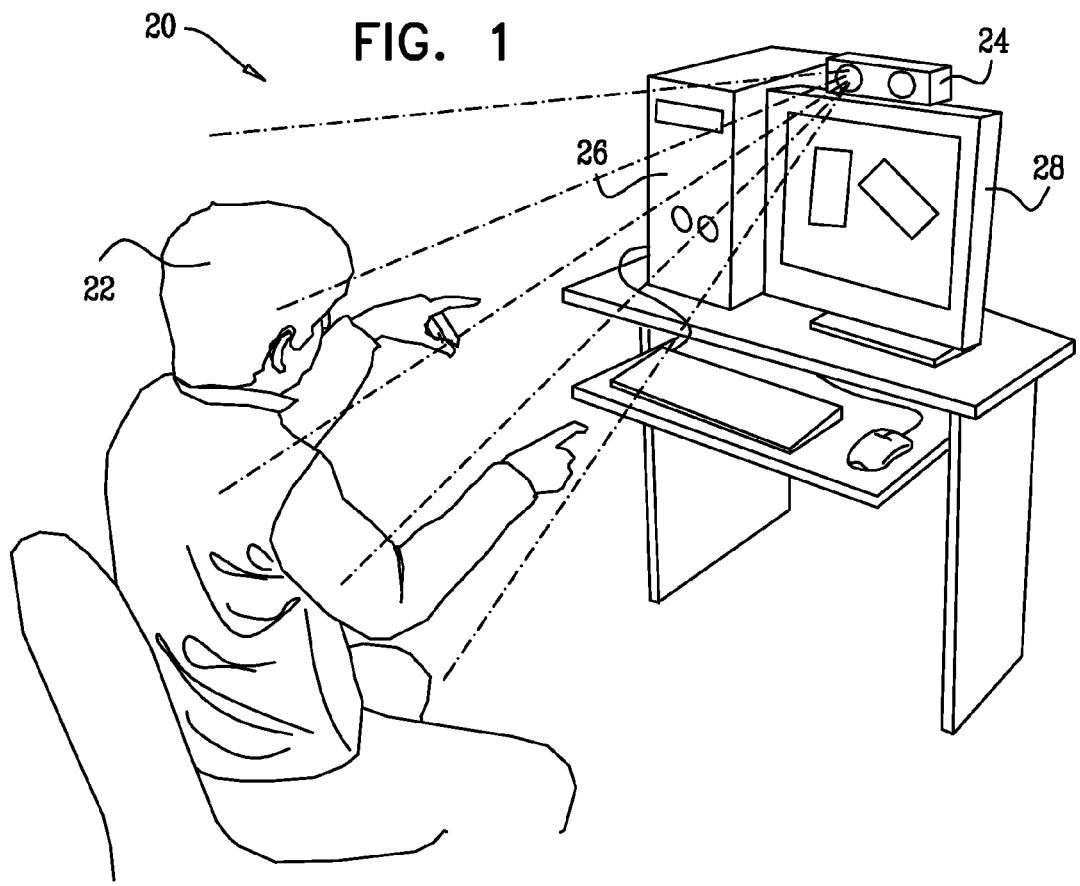
FIG. 1 is a schematic, pictorial illustration of a 3D user interface for a computer system, in accordance with an embodiment of the present invention.

FIG. 1 is a schematic, pictorial illustration of a 3D user interface 20 for operation by a user 22 of a computer 26, in accordance with an embodiment of the present invention. The user interface is based on a 3D sensing device 24, which captures 3D scene information that includes the body (or at least parts of the body) of the user. Device 24 or a separate camera (not shown in the figures) may also capture video images of the scene. The information captured by device 24 is processed by computer 26, which drives a display screen 28 accordingly.

Computer 26 processes data generated by device 24 in order to reconstruct a 3D map of user 22. The term "3D map" refers to a set of 3D coordinates representing the surface of a given object, in this case the user's body. In one embodiment, device 24 projects a pattern of spots onto the object and captures an image of the projected pattern. Computer 26 then computes the 3D coordinates of points on the surface of the user's body by triangulation, based on transverse shifts of the spots in the pattern. Methods and devices for this sort of triangulation-based 3D mapping using a projected pattern are described, for example, in PCT International Publications WO 2007/043036, WO 2007/105205 and WO 2008/120217, whose disclosures are incorporated herein by reference. Alternatively, system 20 may use other methods of 3D mapping, using single or multiple cameras or other types of sensors, as are known in the art.

Computer 26 typically comprises a general-purpose computer processor, which is programmed in software to carry out the functions described hereinbelow. The software may be downloaded to the processor in electronic form, over a network, for example, or it may alternatively be provided on tangible media, such as optical, magnetic, or electronic memory media. Alternatively or additionally, some or all of the functions of the image processor may be implemented in dedicated hardware, such as a custom or semi-custom integrated circuit or a programmable digital signal processor (DSP). Although computer 26 is shown in FIG. 1, by way of example, as a separate unit from sensing device 24, some or all of the processing functions of the computer may be performed by suitable dedicated circuitry within the housing of the sensing device or otherwise associated with the sensing device.

As another alternative, these processing functions may be carried out by a suitable processor that is integrated with display screen 28 (in a television set, for example) or with any other suitable sort of computerized device, such as a game console or media player. The sensing functions of device 24 may likewise be integrated into the computer or other computerized apparatus that is to be controlled by the sensor output.

Figure 2:
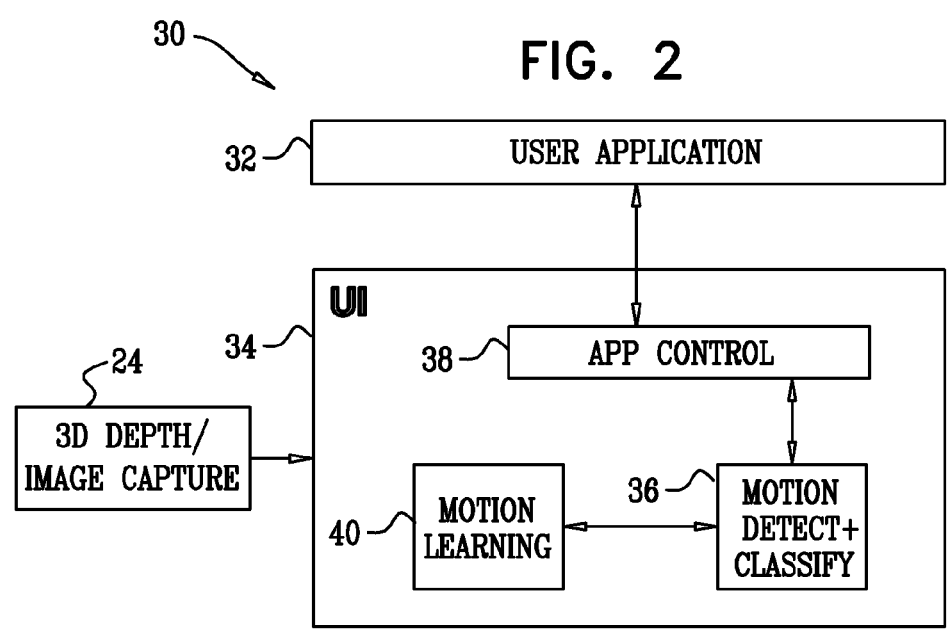
FIG. 2 is a block diagram that schematically illustrates functional components of a 3D user interface, in accordance with an embodiment of the present invention.

FIG. 2 is a block diagram that schematically illustrates a functional structure 30 of system 20, including functional components of a 3D user interface 34, in accordance with an embodiment of the present invention. The operation of these components is described in greater detail with reference to the figures that follow.

User interface 34 receives depth maps based on the data generated by device 24, as explained above. A motion detection and classification function 36 identifies parts of the user's body. It detects and tracks the motion of these body parts in order to decode and classify user gestures as the user interacts with display 28. A motion learning function 40 may be used to train the system to recognize particular gestures for subsequent classification. The detection and classification function outputs information regarding the location and/or velocity (speed and direction of motion) of detected body parts, and possibly decoded gestures, as well, to an application control function 38, which controls a user application 32 accordingly.

Figure 3:
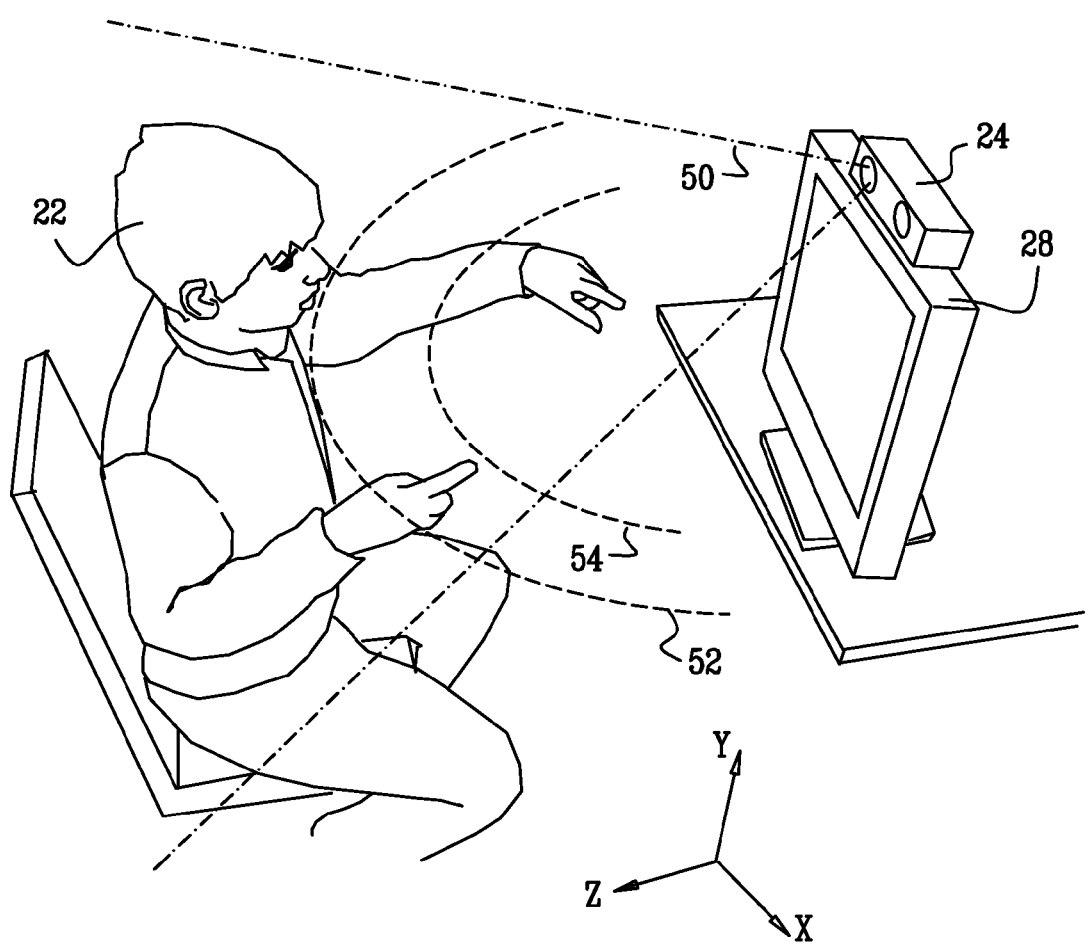
FIG. 3 is a schematic, pictorial illustration showing visualization and interaction regions associated with a 3D user interface, in accordance with an embodiment of the present invention.

FIG. 3 is a schematic, pictorial illustration showing how user 22 may operate a "touchless touch screen" function of the 3D user interface in system 20, in accordance with an embodiment of the present invention. For the purpose of this illustration, the X-Y plane is taken to be parallel to the plane of display screen 28, with distance (depth) perpendicular to this plane corresponding to the Z-axis, and the origin located at device 24. The system creates a depth map of objects within a field of view 50 of device 24, including the parts of the user's body that are in the field of view.

The operation of 3D user interface 34 is based on an artificial division of the space within field of view 50 into a number of regions:

- A visualization surface 52 defines the outer limit of a visualization region. Objects beyond this limit (such as the user's head in FIG. 3) are ignored by user interface 34. When a body part of the user is located within the visualization surface, the user interface detects it and provides visual feedback to the user regarding the location of that body part, typically in the form of an image or icon on display screen 28. In FIG. 3, both of the user's hands are in the visualization region.
- An interaction surface 54, which is typically located within the visualization region, defines the outer limit of the interaction region. When a part of the user's body crosses the interaction surface, it can trigger control instructions to application 32 via application control function 38, as would occur, for instance, if the user made physical contact with an actual touch screen. In this case, however, no physical contact is required to trigger the action. In the example shown in FIG. 3, the user's left hand has crossed the interaction surface and may thus interact with application objects.

The interaction and visualization surfaces may have any suitable shapes. For some applications, the inventors have found spherical surfaces to be convenient, as shown in FIG. 3. Alternatively, one or both of the surfaces may be planar.

Various methods may be used to determine when a body part has crossed interaction surface 54 and where it is located. For simple tasks, static analysis of the 3D locations of points in the depth map of the body part may be sufficient. Alternatively, dynamic, velocity-based detection may provide more timely, reliable results, including prediction of and adaptation to user gestures as they occur. Thus, when a part of the user's body moves toward the interaction surface for a sufficiently long time, it is assumed to be located within the interaction region and may, in turn, result in objects being moved, resized or rotated, or otherwise controlled depending on the motion of the body part.

Additionally or alternatively, the user may control application objects by performing distinctive gestures, such as a "grabbing" or "pushing" motion over an object. The 3D user interface may be programmed to recognize these gestures only when they occur within the visualization or interaction region. Alternatively, the gesture-based interface may be independent of these predefined regions. In either case, the user trains the user interface by performing the required gestures. Motion learning function 40 tracks these training gestures, and is subsequently able to recognize and translate them into appropriate system interaction requests. Any suitable motion learning and classification method that is known in the art, such as Hidden Markov Models or Support Vector Machines, may be used for this purpose.

The use of interaction and visualization surfaces 54 and 52 enhances the reliability of the 3D user interface and reduces the likelihood of misinterpreting user motions that are not intended to invoke application commands. For instance, a circular palm motion may be recognized as an audio volume control action, but only when the gesture is made inside the interaction region. Thus, circular palm movements outside the interaction region will not inadvertently cause volume changes. Alternatively, the 3D user interface may recognize and respond to gestures outside the interaction region.

Analysis and recognition of user motions may be used for other purposes, such as interactive games. Techniques of this sort are described in the above-mentioned U.S. Provisional Patent Application 61/020,754. In one embodiment, user motion analysis is used to determine the speed, acceleration and direction of collision between a part of the user's body, or an object held by the user, and a predefined 3D shape in space. For example, in an interactive tennis game, the computer may translate motion parameters, extracted over time, into certain racket motions, and may identify collisions between the "racket" and the location of a "ball." The computer then changes and displays the direction and speed of motion of the ball accordingly.

Further additionally or alternatively, 3D user interface 34 may be configured to detect static postures, rather than only dynamic motion. For instance, the user interface may be trained to recognize the positions of the user's hands and the forms they create (such as "three fingers up" or "two fingers to the right" or "index finger forward"), and to generate application control outputs accordingly.

Similarly, the 3D user interface may use the posture of certain body parts (such as the upper body, arms, and/or head), or even of the entire body, as a sort of "human joystick" for interacting with games and other applications. For example, the computer may extract the pitch, yaw and roll of the user's upper body and may use these parameters in controlling a flight simulator. Other applications will be apparent to those skilled in the art.

Figure 4:
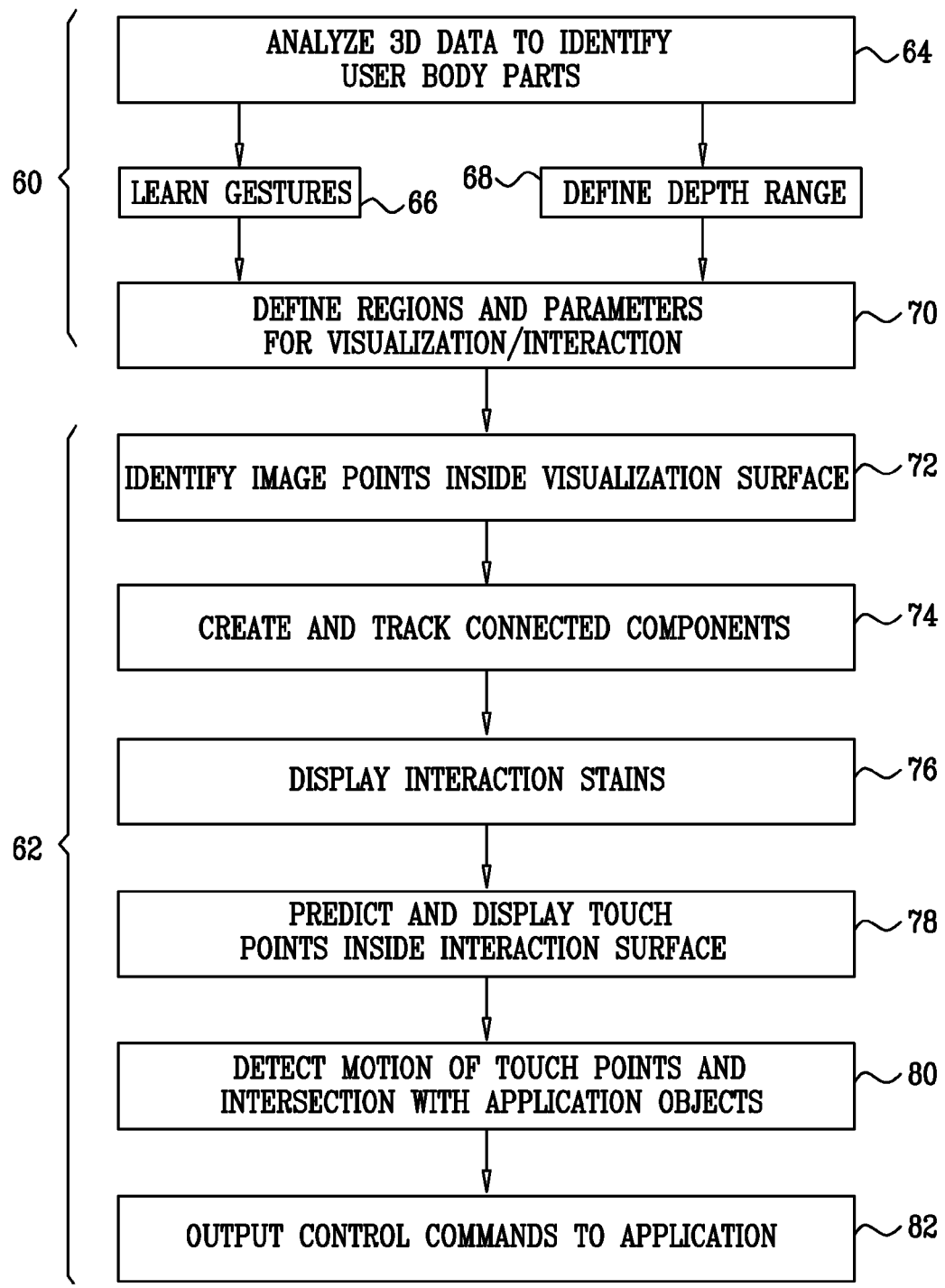
FIG. 4 is a flow chart that schematically illustrates a method for operating a 3D user interface, in accordance with an embodiment of the present invention.

FIG. 4 is a flow chart that schematically illustrates a method for operation of 3D user interface 34, in accordance with an embodiment of the present invention. In this example, the operation is assumed to include a training phase 60, prior to an operational phase 62. During the training phase, the user positions himself (or herself) within field of view 50. Device 24 captures 3D data so as to generate 3D maps of the user's body. Computer 26 analyzes the 3D data in order to identify parts of the user's body that will be used in application control, in an identification step 64. Methods for performing this sort of analysis are described, for example, in PCT International Publication WO 2007/132451, whose disclosure is incorporated herein by reference. The 3D data may be used at this stage in learning user gestures and static postures, as described above, in a gesture learning step 66.

The user may also be prompted to define the limits of the visualization and interaction regions, at a range definition step 68. The user may specify not only the depth (Z) dimension of the visualization and interaction surfaces, but also the transverse (X-Y) dimensions of these regions, thus defining an area in space that corresponds to the area of display screen 28. In other words, when the user's hand is subsequently located inside the interaction surface at the upper-left corner of this region, it will interact with objects at the upper-left corner of the display screen, as though the user were touching that location on a touch screen.

Based on the results of steps 66 and 68, learning function 40 defines the regions and parameters to be used in subsequent application interaction, at a parameter definition step 70. The parameters typically include, inter alia, the locations of the visualization and interaction surfaces and, optionally, a zoom factor that maps the transverse dimensions of the visualization and interaction regions to the corresponding dimensions of the display screen.

During operational phase 62, computer 26 receives a stream of depth data from device 24 at a regular frame rate, such as thirty frames/sec. For each frame, the computer finds the geometrical intersection of the 3D depth data with the visualization surface, and thus extracts the set of points that are inside the visualization region, at an image identification step 72. This set of points is provided as input to a 3D connected component analysis algorithm (CCAA), at an analysis step 74. The algorithm detects sets of pixels that are within a predefined distance of their neighboring pixels in terms of X, Y and Z distance. The output of the CCAA is a set of such connected component shapes, wherein each pixel within the visualization plane is labeled with a number denoting the connected component to which it belongs. Connected components that are smaller than some predefined threshold, in terms of the number of pixels within the component, are discarded.

CCAA techniques are commonly used in 2D image analysis, but changes in the algorithm are required in order to handle 3D map data. A detailed method for 3D CCAA is presented in the Appendix below. This kind of analysis reduces the depth information obtained from device 24 into a much simpler set of objects, which can then be used to identify the parts of the body of a human user in the scene, as well as performing other analyses of the scene content.

Computer 26 tracks the connected components over time. For each pair of consecutive frames, the computer matches the components identified in the first frame with the components identified in the second frame, and thus provides time-persistent identification of the connected components. Labeled and tracked connected components, referred to herein as "interaction stains," are displayed on screen 28, at a display step 76. This display provides user 22 with visual feedback regarding the locations of the interaction stains even before there is actual interaction with application objects. Typically, the computer also measures and tracks the velocities of the moving interaction stains in the Z-direction, and possibly in the X-Y plane, as well.

Computer 26 detects any penetration of the interaction surface by any of the interaction stains, and identifies the penetration locations as "touch points," at a penetration detection step 78. Each touch point may be represented by the center of mass of the corresponding stain, or by any other representative point, in accordance with application requirements. The touch points may be shown on display 28 in various ways, for example:

As a "static" shape, such as a circle at the location of each touch point;

As an outline of the shape of the user's body part (such as the hand) that is creating the interaction stain, using an edge detection algorithm followed by an edge stabilization filter;

As a color video representation of the user's body part. Furthermore, the visual representation of the interaction stains may be augmented by audible feedback (such as a "click" each time an interaction stain penetrates the visualization or the interaction surface). Additionally or alternatively, computer 26 may generate a visual indication of the distance of the interaction stain from the visualization surface, thus enabling the user to predict the timing of the actual touch.

Further additionally or alternatively, the computer may use the above-mentioned velocity measurement to predict the appearance and motion of these touch points. Penetration of the interaction plane is thus detected when any interaction stain is in motion in the appropriate direction for a long enough period of time, depending on the time and distance parameters defined at step 70.

Optionally, computer 26 applies a smoothing filter to stabilize the location of the touch point on display screen 28. This filter reduces or eliminates random small-amplitude motion around the location of the touch point that may result from noise or other interference. The smoothing filter may use a simple average applied over time, such as the last N frames (wherein N is selected empirically and is typically in range of 10-20 frames). Alternatively, a prediction-based filter can be used to extrapolate the motion of the interaction stain. The measured speed of motion of the interaction stain may be combined with a prediction filter to give different weights to the predicted location of the interaction stain and the actual measured location in the current frame.

Computer 26 checks the touch points identified at step 78 against the locations of application objects, at an intersection checking step 80. Typically, when a touch point intersects with a given object, it selects or activates the object, in a manner analogous to touching an object on a touch screen.

Figure 5:
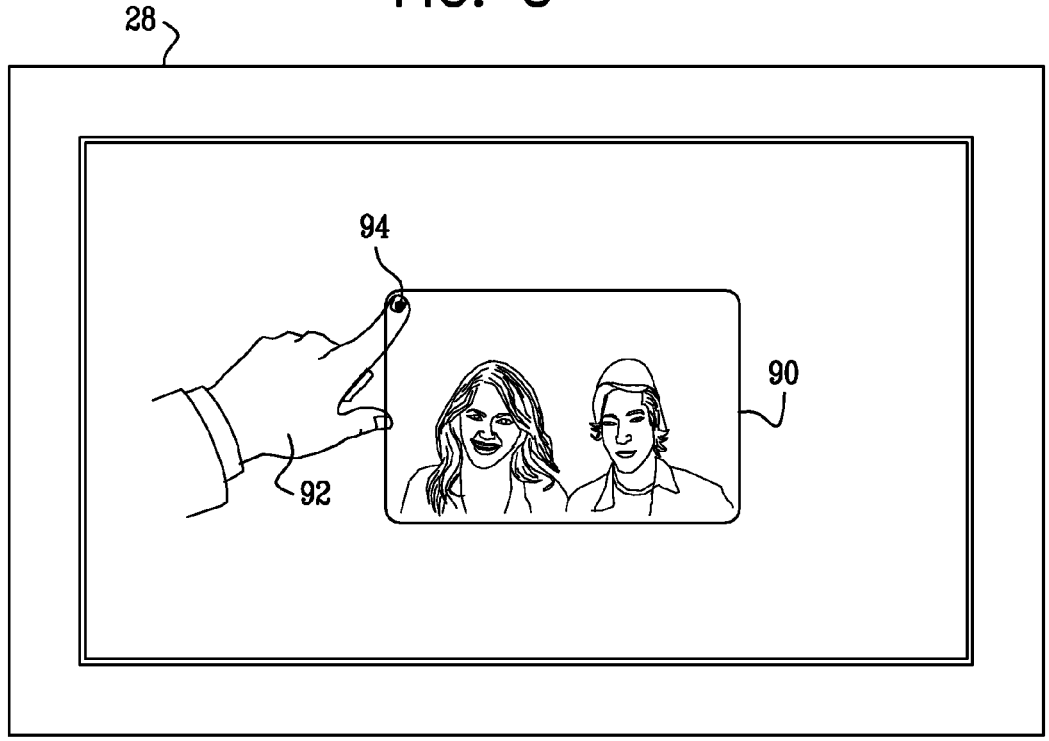
FIG. 5 is a schematic representation of a computer display screen, showing images created on the screen in accordance with an embodiment of the present invention.

FIG. 5 is a schematic representation of display screen 28, showing images created on the screen by the method described above, in accordance with an embodiment of the present invention. In this example, application 32 is a picture album application, in which the object to be manipulated by the user is a photo image 90. An interaction stain 92 represents the user's hand. A touch point 94 represents the user's index finger, which has penetrated the interaction surface. (Although only a single touch point is shown in this figure for the sake of simplicity, in practice there may be multiple touch points, as well as multiple interaction stains.) When an active touch point is located within the boundary of photo image 90, as shown in the figure, the photo image may "stick" itself to the touch point and will then move as the user moves the touch point. When two touch points (corresponding to two of the user's fingers, for example) intersect with a photo image, their motion may be translated into a resize and/or rotate operation to be applied to the photo image.

Additionally or alternatively, a user gesture, such as "grab," "push," or "pull" may be required to verify the user's intention to activate an object. Computer 26 may recognize simple hand gestures by applying a motion detection algorithm to one or more interaction stains located within the interaction region or the visualization region. For example, the computer may keep a record of the position of each stain record over the past N frames, wherein N is defined empirically and depends on the actual length of the required gesture. (With a 3D sensor providing depth information at 30 frames per second, N=10 gives good results for short, simple gestures.) Based on the location history of each interaction stain, the computer finds the direction and speed of motion using any suitable fitting method, such as least-squares linear regression. The speed of motion may be calculated using timing information from any source, such as the computer's internal clock or a time stamp attached to each frame of depth data, together with measurement of the distance of motion of the interaction stain.

Returning now to FIG. 4, computer 26 generates control commands for the current application based on the interaction of the touch points with application objects, as well as any appropriate gestures, at a control output step 82. The computer may associate each direction of movement of a touch point with a respective action, depending on application requirements. For example, in a media player application, "left" and "right" movements of the touch point may be used to control channels, while "up" and "down" control volume. Other applications may use the speed of motion for more advanced functions, such as "fast down" for "mute" in media control, and "fast up" for "cancel."

More complex gestures may be detected using shape matching. Thus "clockwise circle" and "counterclockwise circle" may be used for volume control, for example. (Circular motion may be detected by applying a minimum-least-square-error or other fitting method to each point on the motion trajectory of the touch point with respect to the center of the circle that is defined by the center of the minimal bounding box containing all the trajectory points.) Other types of shape learning and classification may use shape segment curvature measurement as a set of features for a Support Vector Machine computation or for other methods of classification that are known in the art.

Although certain embodiments of the present invention are described above in the context of a particular hardware configuration and interaction environment, as shown in FIG. 1, the principles of the present invention may similarly be applied in other types of 3D sensing and control systems, for a wide range of different applications. The terms "computer" and "computer application," as used in the present patent application and in the claims, should therefore be understood broadly to refer to any sort of computerized device and functionality of the device that may be controlled by a user.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

APPENDIX

Connected Component (3DCC) Analysis

In an embodiment of the present invention, the definition of a 3DCC is as follows:

Two 3D points are said to be D-connected to each other if their projections on the XY plane are located next to each other, and their depth values differ by no more than a given threshold D_TH.

Given two 3D points P and Q, there is said to be a D-connected path between them if there exists a set of 3D points (P, p1, p2, ... pN, Q) such that each two consecutive points in the list are D-connected to each other.

A set of 3D points is said to be D-connected if any two points within it have a D-connected path between them.

A D-connected set of 3D points is said to be maximally D-connected if for each point p within the set, no neighbor of p in the XY plane can be added to the set without breaking the connectivity condition.

In one embodiment of the present invention, the 3DCCA algorithm finds maximally D-connected components as follows:
1. Allocate a label value for each pixel, denoted by LABEL (x,y) for the pixel located at (x,y).
2. Define a depth threshold D_TH.
3. Define a queue (first in—first out) data structure, denoted by QUEUE.
4. Set LABEL(x,y) to be −1 for all x,y.
5. Set cur_label to be 1.
6. START: Find the next pixel p-start whose LABEL is −1. If there are no more such pixels, stop.
7. Set LABEL(p_start) to be cur_label and increment cur_label by one.
8. Insert the pixel p_start into QUEUE.
9. While the QUEUE is not empty, repeat the following steps:
   a. Remove the head item (p_head=x,y) from the queue.
   b. For each neighbor N of p_head:
      i. if LABEL(N) is >0 skip to the next neighbor.
      ii. if the depth value of N differs from the depth value of p_head by no more than D_TH, add p_head to the queue and set LABEL(p_head) to be cur_label.
10. Goto START In the above algorithm, the neighbors of a pixel (x,y) are taken to be the pixels with the following coordinates: (x−1, y−1), (x−1, y), (x−1, y+1), (x, y−1), (x, y+1), (x+1, y−1), (x+1, y), (x+1, y+1). Neighbors with coordinates outside the bitmap (negative or larger than the bitmap resolution) are not taken into consideration.

Performance of the above algorithm may be improved by reducing the number of memory access operations that are required. One method for enhancing performance in this way includes the following modifications:
   Another data structure BLOBS is maintained, as a one-dimensional array of labels. This data structure represents the lower parts of all connected components discovered in the previous iteration. BLOBS is initialized to an empty set.
   In step 9b above, instead of checking all neighbors of each pixel, only the left and right neighbors are checked.
   In an additional step 9c, the depth differences between neighboring values in the BLOBS structure are checked, in place of checking the original upper and lower neighbors of each pixel in the depth map.

The invention claimed is:

1. A user interface method, comprising:
displaying an object on a display screen;
defining an interaction surface containing an interaction region in space, and mapping the interaction surface to the display screen;
capturing a sequence of depth maps over time of at least a part of a body of a human subject;
processing the depth maps in order to detect a direction and speed of movement of the part of the body and to predict a touch point of the part of the body, responsively to the movement, wherein the touch point indicates a location in the interaction surface where the part of the body penetrates the interaction surface;
controlling a computer application so as to change the displayed object on the screen responsively to the mapping and to the predicted touch point; and
wherein processing the depth maps comprises identifying, responsively to the detected movement, a collision induced by the movement with a predefined three-dimensional shape in space.

2. The method according claim 1, and comprising:
defining a visualization surface containing a visualization region in the space, such that the interaction surface is within the visualization region; and
processing the depth maps in order to identify the part of the body that is located within the visualization region, wherein displaying the object comprises presenting on the display screen a representation of the part of the body that is located within the visualization region.

3. The method according claim 1, wherein defining the interaction surface comprises specifying dimensions of the interaction surface, wherein the interaction surface is mapped to the display screen responsively to the specified dimensions.

4. The method according to claim 1, wherein processing the depth maps comprises applying a three-dimensional connected component analysis to the depth maps in order to identify the part of the body.

5. The method according to claim 1, wherein processing the depth maps comprises identifying, responsively to the detected movement, a gesture made by the human subject.

6. The method according to claim 5, wherein identifying the gesture comprises learning the gesture during a training phase, and thereafter detecting the learned gesture in order to control the computer application.

7. The method according to claim 1, wherein processing the depth maps comprises identifying a posture of at least the part of the body, and controlling the computer application responsively to the posture.

8. User interface apparatus, comprising:
a display screen, which is configured to display an object;
a sensing device, which is configured to capture a sequence of depth maps over time of at least a part of a body of a human subject;
a processor, which is configured to define an interaction surface, which contains an interaction region in space, and to map the interaction surface to the display screen, and to process the depth maps in order to detect a direction and speed of movement of the part of the body and to predict a touch point of the part of the body, responsively to the movement, wherein the touch point indicates a location in the interaction surface where the part of the body penetrates the interaction surface and to control a computer application so as to change the displayed object on the screen responsively to the mapping and to the predicted touch point; and
wherein processing the depth maps comprises identifying, responsively to the detected movement, a collision induced by the movement with a predefined three-dimensional shape in space.

9. The apparatus according claim 8, wherein the processor is configured to process the depth maps in order to identify the part of the body that is located within a visualization region contained within a predefined visualization surface, such that the interaction surface is within the visualization region, and to present on the display screen a representation of the part of the body that is located within the visualization region.

10. The apparatus according claim 8, wherein the processor is configured to accept a specification of dimensions of the interaction surface, and to map the interaction surface to the display screen responsively to the dimensions.

11. The apparatus according to claim 8, wherein the processor is configured to apply a three-dimensional connected component analysis to the depth maps in order to identify the part of the body.

12. The apparatus according to claim 8, wherein the processor is configured to identify, responsively to the detected movement, a gesture made by the human subject.

13. The apparatus according to claim 12, wherein the processor is configured to learn the gesture during a training phase, and thereafter to detect the learned gesture in order to control the computer application.

14. A computer software product, comprising a computer-readable medium in which program instructions are stored, which instructions, when read by a computer,
cause the computer to display an object on a display screen,
to define an interaction surface, which contains an interaction region in space, and to map the interaction surface to the display screen,
to process a sequence of depth maps created over time of at least a part of a body of a human subject in order to detect a direction and speed of movement of the part of the body and to predict a touch point of the part of the body, responsively to the movement, wherein the touch point indicates a location in the interaction surface where the part of the body penetrates the interaction surface,
to control a computer application so as to change the displayed object on the screen responsively to the mapping and to the predicted touch point, and
wherein processing the depth maps comprises identifying, responsively to the detected movement, a collision induced by the movement with a predefined three-dimensional shape in space.

15. The method according to claim 1, wherein defining the interaction surface comprises receiving an input from a user of the computer application, and defining the interaction surface responsively to the input.

16. A user interface method, comprising:
displaying an object on a display screen;
defining, responsively to an input received from a user of the computer application, an interaction surface containing an interaction region in space for a computer application while specifying, based on the input received from the user, dimensions in space of the interaction region that correspond to an area of the display screen;
capturing a sequence of depth maps over time of at least a part of a body of a human subject;
processing the depth maps in order to detect a movement of the part of the body as the part of the body passes through the interaction surface;
controlling the computer application so as to change the displayed object on the screen responsively to the movement of the part of the body within the specified dimensions of the interaction region; and
wherein processing the depth maps comprises identifying, responsively to the detected movement, a collision induced by the movement with a predefined three-dimensional shape in space.

17. The method according to claim 16, wherein the input received from the user specifies a depth dimension of the interaction surface.

18. The method according to claim 17, wherein the input received from the user also specifies transverse dimensions of the interaction surface.

19. The method according to claim 16, wherein specifying the dimensions in space comprises defining a zoom factor that maps transverse dimensions of the interaction surface to corresponding dimensions of the computer display screen.

* * * * *